United States Patent [19]

Yates

[11] 4,443,638

[45] Apr. 17, 1984

[54] PREPARATION OF ALCOHOLS FROM INTERNAL OLEFINS

[75] Inventor: James A. Yates, Ponca City, Okla.

[73] Assignee: Conoco, Inc., Ponca City, Okla.

[21] Appl. No.: 369,953

[22] Filed: Apr. 19, 1982

Related U.S. Application Data

[63] Continuation of Ser. No. 250,977, Apr. 3, 1981, abandoned.

[51] Int. Cl.$^3$ .............................................. C07C 29/14
[52] U.S. Cl. .................................. 568/882; 568/454; 568/914
[58] Field of Search ......................... 568/454, 882, 914

[56] References Cited

U.S. PATENT DOCUMENTS

| | | | |
|---|---|---|---|
| 2,638,487 | 5/1953 | Russum et al. | 568/882 |
| 3,501,537 | 3/1970 | Johnson et al. | 568/914 |
| 3,933,919 | 1/1976 | Wilkinson | 568/454 |
| 4,148,830 | 4/1979 | Pruett et al. | 568/454 |
| 4,158,020 | 6/1979 | Stautzenberger | 568/454 |
| 4,190,731 | 2/1980 | Nehring et al. | 568/914 |
| 4,299,990 | 11/1981 | Tummes et al. | 568/454 |

OTHER PUBLICATIONS

Iriuchijima et al., Chem. Abs. 77:131259d.
Evans et al., Jour Chem. Soc. (A), (1968), 3133–3142.

Primary Examiner—Bernard Helfin
Attorney, Agent, or Firm—Robin M. Davis

[57] ABSTRACT

A process for preparing alcohols from internal olefins is disclosed. Briefly, the process comprises (a) hydroformylation of internal olefins to aldehydes using a small amount of a ligand modified recycled rhodium catalyst, (b) separating the reaction product from the catalyst by flash vacuum distillation, (c) hydrogenating the aldehydes to form a product containing alcohols, and (d) removing impurities and recovering the desired alcohol product. An important feature of this process, centers around the use of internal olefins to make an alcohol product which has a large amount of linear alcohol and 2-methyl-branched alcohol in the product.

8 Claims, No Drawings

PREPARATION OF ALCOHOLS FROM INTERNAL OLEFINS

This is a continuation in part of the application filed on April 3, 1981, Serial No. 250,977.

FIELD OF THE INVENTION

The invention is in the general field of preparing alcohols from olefins; more specifically, however, this invention relates to the use of solely internal olefins for this purpose.

GENERAL BACKGROUND

Alcohols have been prepared from olefins by the oxo reaction using cobalt carbonyl catalyst either unmodified or modified with a coordinating ligand such as a phosphine. The alcohol product depends on nature of the starting olefin, the reaction conditions, and nature of the cobalt catalyst system. The major side products of the cobalt system are paraffin (from hydrogenation of starting olefin) and heavies. The phosphine modified cobalt system produces mostly paraffin as a side product whereas the unmodified system gives mostly heavies. In either case the alcohol yield is around 80% of the theoretical value.

More recently, processes have been developed which use rhodium as the hydroformylation catalyst. Most of these use phosphorus containing ligands as catalyst modifiers; however, some do not. Most of the published information about the rhodium catalyst system deals with converting alpha olefins to aldehydes and subsequently to alcohols that contain very high proportions of the linear isomer.

One of these rhodium catalyst systems is concerned with a process for making n-butylaldehyde from propene with a rhodium triphenyl phosphine catalyst system. That process uses a large excess of the phosphine ligand relative to the amount of rhodium present. In general, most rhodium catalyzed oxo systems use a rhodium concentration, based on olefins, in the range of 100–1,000 parts per million based on the feed.

Since rhodium is extremely expensive the rhodium catalyst system suffers a significant economic disadvantage.

I have discovered that recycled rhodium in small concentrations can be used as a catalyst in hydroformylation processes which employ internal olefins to get a substantial amount of linear and 2-methyl-branched aldehydes and/or alcohols. Still further, I have found that the rhodium can be recovered for recycling using a relatively simple flash distillation, and, even more unexpectedly, that the recycled rhodium is a more active catalyst than the original.

Rhodium has been known in the art to be useful for the preparation of aldehydes and alcohols from olefins using hydroformylation. Two U.S. patents which depict this are U.S. Pat. No. 4,299,990 and U.S. Pat. No. 3,933,919. Both of these patents, however, use rhodium in large concentrations. Specifically, in U.S. Pat. No. 4,299,990 the rhodium is in concentrations of 0.01% per weight of olefin, or better described in terms of parts per million, as 100 parts per million based on the olefin feed. U.S. Pat. No. 3,933,919 calls for rhodium in concentrations of 1,000 parts per million. Not only does the instant invention necessitate much smaller concentrations of rhodium but it also would not operate at concentrations this large. Available relevant data indicates that at higher rhodium concentrations the product yield from hydroformylation of internal olefins will be mainly heavily-branched aldehyde and alcohol material. Thus, these two patents teach away from the instant invention since the instant invention uses small concentrations of rhodium to produce aldehydes and alcohols that overall are more linear. More specifically, there is a substantial portion of the product that is linear and 2-methyl-branched aldehyde and alcohol.

U.S. Pat. No. 4,299,990 calls for a temperature range from 80° C. to 160° C. and U.S. Pat. No. 3,933,919 provides for a temperature range of 50° C. to 150° C.; and U.S. Pat. No. 4,148,830 provides for a temperature range of 50° C. to 145° C. These temperature ranges are, overall, too low for a feed stock of internal olefins, as in the case of the instant invention, when a more linear product is desired. When internal olefins are used, higher temperatures are necessitated.

In contrast, using temperatures called for in the instant invention, internal olefins will undergo extensive isomerization, and as a result, a larger variety of isomeric aldehyde are obtained. At the higher temperatures, the process becomes even more selective to the production of more linear isomers. Even more surprising and desirable is the higher concentration of linear aldehyde in the product. Much more linear aldehyde is formed than would be expected from an equilibrium mixture of olefin isomers as long as these high temperatures are maintained. Pressure must be carefully controlled. In the instant invention, higher pressures are necessitated to prevent catalyst decomposition at the temperatures required. Thus, due to carefully controlled inter-relating conditions, the instant invention enables hydroformylation of internal olefinic product with low rhodium concentrations which will yield a more linear product. The advantages of the instant invention are illustrated by contrast to previous art. The present invention provides the economic advantage of having low rhodium concentrations, the advantage of being able to use an exclusively internal olefin feed, and also the advantage of obtaining a more linear product. Other advantages, however, will become apparent to those skilled in the art as the description proceeds.

BRIEF SUMMARY OF THE INVENTION

A process for preparing alcohols from $C_4$–$C_{30}$ internal olefins wherein said process comprises:

(a) contacting said internal olefins with hydrogen and carbon monoxide in the presence of a ligand-modified recycled rhodium catalyst where the rhodium concentration is no greater than 20 parts per million based on total feed (which is substantially totally internal ofefin for the first cycle) at temperatures in the range of about 145° C. to about 180° C. and pressures in the range of about 750 to about 2,000 psig to form a reaction product containing a substantial amount of aldehydes, a substantial portion of which is linear and 2-methyl-branched aldehyde;

(b) separating the reaction product of step (a) from the rhodium catalyst by flash vacuum distillation;

(c) hydrogenating the distilled reaction product of step (b) using an effective amount of hydrogenation catalyst at temperatures in the range of 100° to about 170° C. and pressures in the range of about 200 to about 2,000 psig to produce a crude alcohol mixture, (d) fractionally distilling the crude alcohol mixture of step (c) to remove small amounts of light and heavy impurities and obtain a fraction containing a major amount of alcohols and minor amounts of carbonyl compounds, and;

(e) hydrogenating the fraction containing alcohols and carbonyls using the conditions of step (c) to convert the carbonyl compounds to alcohols and thereby obtaining a product consisting totally of alcohols;

(f) recycling the product-catalyst bottoms from step (b) to step (a).

DETAILED DESCRIPTION

Suitable olefins for use in my process contain from 4 to about 30 carbon atoms and are internal olefins so that the olefin bond is randomly located throughout the hydrocarbon chain. While linear olefins are desirable, branched and linear olefins are suitable. However, if branched olefin is used, the double bond should be at least one carbon removed from the branch in the chain. The preferred olefins contain from about 6 to about 15 carbon atoms.

Ligand modified rhodium catalysts are well-known in the art. These catalysts are a complex of a rhodium compound and a ligand containing a trivalent atom of a Group VA element including phosphorous, arsenic and antimony, said trivalent atom possessing one available pair of electrons. Suitable rhodium compounds are the oxides and salts of rhodium, with the oxides being preferred. The most preferred rhodium compound is $Rh_2O_3.5H_2O$.

Suitable ligands include the trialkylphosphites, the tricycloalkylphosphites, and triarylphosphites, the triarylphosphines, the trialkyl phosphines, the triarylstibines, and the triarylarsines. Desirably each organo moiety in the ligand does not exceed 18 carbon atoms. The triarylphosphites and the triarylphosphines represent the preferred classes of ligands. Specific examples of ligands which are suitable in forming the complex catalysts include trimethylphosphite, triethylphosphite, butyldiethylphosphite, tri-n-propylphosphite, tri-n-butylphosphite, tri-2-ethylhexylphosphite, tri-n-octylphosphite, tri-n-doceylphosphite, triphenylphosphite, trinaphyphosphite, triphenylphosphine, tributylphosphine, trioctylphosphine, tri(p-chlorophenyl)phosphite, trinapthylphosphine, phenyl diphenylphosphinite, diphenyl phenylphosphonite, diphenyl ethylphosphonite, tri-phenylarsine, triphenylstibine, tris-(p-chlorophenyl)-phosphine, tri(P-cyanophenyl)phosphite, tris (p-methoxyphenyl)phosphite, ethyl diphenylphosphinite, and the like. Triphenylphosphite and trioctylphosphine are examples of the most preferred ligands.

The relative amounts of rhodium compound and ligand in the complex, on a molar basis, are in the range of about 1:0.5 to 1:10, preferably about 1:2 to 1:4 (rhodium to ligand).

Any conventional hydrogenation catalyst can be used in the hydrogenation steps of my process. Nickel is a particularly suitable catalyst. An example of a particularly suitable catalyst is a supported nickel catalyst containing about 50 to 60 weight percent nickel on an alumina support.

Step (a) of my process, i.e., the hydroformylation of the internal olefins, is conducted under the conditions listed in Table 1.

TABLE 1

|  | Suitable | Preferred |
|---|---|---|
| Temperature, °C. | 145–180 | 145–165 |
| Pressure, psig | 750–2000 | 850–1200 |
| $H_2$—CO, mole ratio | 0.5–2.0 | 0.9–1.1 |

TABLE 1-continued

|  | Suitable | Preferred |
|---|---|---|
| Amount of catalyst ppm Rh based on total feed (100% internal olefin at the beginning of the first cycle) | 1–20 | 5–15 |
| Reaction Time (Hours) | 1–10 | 2–6 |

The procedure for conducting the hydroformylation step of my process is straightforward and will be illustrated by the examples.

At the conclusion of the hydroformylation reaction the reaction product is removed from the rhodium catalyst. Recycle of the rhodium catalyst is an important feature of my process which renders it more attractive economically. While several methods are known for recovering rhodium catalyst from various hydroformylation reactions most are fairly complicated. For example, one process uses a solvent.

I have discovered that the rhodium can be re-used by employing a flash vacuum distillation separation and recycle step. The distillation should be conducted using a short residence time (e.g. 0.25–1 minute). The aldehyde products, along with residual unreacted olefins are in the overhead of the distillation, about 75% of the total product, while the rhodium complex is in the bottoms product of the distillation and is re-used as catalyst in succeeding reactions. In fact when this recycle step is employed, a surprising effect on the overall reaction is noted. Specifically, as is pointed out in Example 2, the recycled catalyst tends to be more active. Thus an important advantage is gained by recycling the catalyst in this manner.

The aldehyde-containing distillate product is then hydrogenated using a typical hydrogenation catalyst (preferably nickel). Preferably, the hydrogenation is conducted on a continuous basis. The conditions for the hydrogenation step are listed in Table 2.

TABLE 2

|  | Suitable | Preferred |
|---|---|---|
| Temperature, °C. | 100–170 | 120–150 |
| Pressure, psig | 200–2000 | 800–1200 |
| Catalyst* | 0.5–2.0 | 0.8–1.2 |

*Gram aldehyde liquid/(gram catalyst) (hour)

Upon completion of the hydrogenation reaction the crude alcohol product is fractionally distilled to remove small amounts of light and heavy impurities. The center cut contains a major amount of alcohols and a minor amount of carbonyl compounds.

The center cut (alcohol) fraction is then hydrogenated to convert the carbonyls to alcohols, using the same conditions which were used in the first hydrogenation. Upon completion of the hydrogenation the desired product is obtained.

In order to illustrate the nature of the present invention still more clearly the following examples will be given. It is to be understood, however, that the invention is not to be limited to the specific conditions or details set forth in these examples except insofar as such limitations are specified in the appended claims.

EXAMPLE 1

This example illustrates the hydroformylation step, in four separate experiments using a catalyst containing fresh $Rh_2O_3.5H_2O$. The procedure was as follows:

30 grams (g) of 7-tetradecene and 5 g of n-dodecane were added to a 100 milliliters (ml) stainless steel magnetically stirred autoclave along with the desired quantity of $Rh_2O_3.5H_2O$ and triphenylphosphite. The autoclave was sealed and flushed several times with the 1:1 $H_2/CO$ gas mixture to be used in the oxo reaction while stirring. The autoclave was pressured to ca 200 psig under the desired operating pressure and then heated to the desired operating temperature. The pressure was then increased to the desired pressure. Samples of the reaction product were taken at various time intervals and analyzed by gas chromatography (GC) with the n-dodecane serving as an internal standard.

Data from four of the experiments carried out are summarized in Table 4. From these data it is apparent that the hydroformylation reaction proceeds at a good rate in the presence of very low levels of catalyst to give excellent yields of aldehydes and some alcohol. The product aldehyde and alcohol contains a significant amount of the linear isomer even though the starting olefin was 7-tetradecene, a single deep internal isomer.

dium catalyst was added. Samples of each crude reaction product were analyzed by gas chromatography (GC) to determine the residual olefin content. Each "Asco" still overhead product was also analyzed by GC to determine its composition. The bottoms product from the fourth cycle was also analyzed by GC. Through these four cycles there was no indication of any loss in catalyst activity. In fact the recycle catalyst was more active than the fresh catalyst.

The four "Asco" overhead products were combined and hydrogenated in a continuous hydrogenation reactor using 1/8"×1/8" tablets of a nickel catalyst (containing ca 58% Ni on an alumina support) and operating at 800 psig $H_2$, 135° C., and a space velocity of 0.61 ml feed/g catalyst/hr. This converted the aldehyde product to a crude alcohol product which was fractionally distilled to give a 5% precut, 86% heart cut, and 9% bottoms (mostly usable alcohol).

The heart cut alcohol was hydrogenated again in the same reactor using the same catalyst and conditions except for the space velocity which as 1.16 ml feed per gram of catalyst per hour.

TABLE 4

| Expt. No. | Rh Conc. (ppm) Based on Internal Olefin Feed | Mole ratio (Ligand) Rh | Temp. (°C.) | Pressure (psig) | Reaction Time (Hr) | Olefin Conv. (%) | Reaction Rate (Hr-) | n-paraffin | Aldehyde | Alcohol | Heavies | Linear Product % |
|---|---|---|---|---|---|---|---|---|---|---|---|---|
| A | 11 | 2 | 150 | 900 | 4 | 99 | 1.2 | 1.5 | 93 | 4.0 | ca 1 | 15.0 |
| B | 25 | 4 | 140 | 950 | 2 | 99 | 3.0 | 0.7 | 97 | 1.2 | ca 1 | 12.5 |
| C | 5 | 4 | 150 | 950 | 5 | 99 | 1.3 | 1.3 | 95 | 2.8 | ca 1 | 15.0 |
| D | 5 | 4 | 140 | 950 | 5 | 99 | 1.3 | 0.8 | 97 | 1.2 | ca 1 | 10.0 |

PRODUCT YIELD (Mole %) spans n-paraffin, Aldehyde, Alcohol, Heavies columns.

EXAMPLE 2

This example illustrates the use of recycled rhodium in my invention.

The process was as follows:

700 g of an isomeric mixture of internal n-decenes was added to a 2 l stirred autoclave (Parr) along with 11.7 mg $Rh_2O_3.5H_2O$ (equivalent to 10 parts per million (ppm) Rh in the system) and 64 (mg) triphenylphosphite. The autoclave was flushed with a 1:1 $H_2/CO$ mixture to remove inert gases present. It was then pressured to 950 psig with the $H_2/CO$ mix and heated to 150° C. When the reaction was complete the product was removed from the reactor and passed through an "Asco" thin film molecular still at 120° C. and 10 mm Hg pressure to give 75–80% overhead and 20–25% bottoms. The bottoms fraction was combined with enough fresh olefin to make another 700 g addition to the oxo reactor. Additional triphenylphosphite (64 mg) was also added to the fresh olefin. This sequence was repeated for a total of four cycles including the initial run. Triphenylphosphite was added to each cycle but no makeup rho- The composition of the finished alcohol is shown in the following table:

| CHEMICAL ANALYSIS | |
|---|---|
| Hydroxyl No. | 321.5 mg KOH/g |
| Acid No. | 0.4 mg KOH/g |
| Sap. No. | 0.8 mg KOH/g |
| Carbonyl | 17.0 ppm CO |
| Iodine No. | 0.03 g $I_2$/100 g |
| KF Water | 0.12% |
| GC* ANALYSIS | |
| Pre $C_{11}$ alcohol | 0.7% |
| 2-Butyl-1-heptanol | 13.3% |
| 2-Propyl-1-octanol | 14.0% |
| 2-Ethyl-1-nonanol | 15.6% |
| 2-Methyl-1-decanol | 34.5% |
| Unidentified intermediates | 0.6% |
| n-Undecanol | 21.3% |

*Gas Chromatography

The results and a material balance for this series of runs are shown in Table 5.

TABLE 5

$C_{10}$ Internal Olefin Catalyst Recycle Study Material Balance

| No. Of Times Catalyst Is Cycled | CHARGE WT. Olefin | CHARGE WT. Recycle | Product Wt. (g) | ASCO DISTILLATION OVH | ASCO DISTILLATION BTM | (g.) L-H | ASCO OVERHEAD COMPOSITION (g) Hydrocarbon | Aldehyde | Alcohol | Unknown | REACTION Time (Hr) | REACTION Conv. % |
|---|---|---|---|---|---|---|---|---|---|---|---|---|
| 1 | 700.0 | — | 812.3 | 672.8 | 132.1 | 2.9 | 65.4 | 557.8 | 37.7 | 11.4 | 5.5 | ca 94 |
| 2 | 574.0 | 132.1 | 825.9 | 658.4 | 163.5 | 4.0 | 19.1 | 587.3 | 46.1 | 5.9 | 5.0 | ca 99 |
| 3 | 539.2 | 163.5 | 832.0 | 627.3 | 203.0 | 0.3 | 15.7 | 546.2 | 44.1 | 23.3 | 4.0 | ca 99 |
| 4 | 497.0 | 203.0 | 804.3 | 611.3 | 192.0 | 1.0 | 17.7 | 534.3 | 48.9 | 10.4 | 4.0 | ca 99 |
| Total | 2310.2 | | | 2571.8 | 192.0 | 7.6 | 118.4 | 2225.6 | 176.8 | 51.0 | | |
| FINAL ASCO BTM Composition (g) | | | | | 192.0 | | 1.2 | 96.8 | 50.7 | 43.3 | | |
| Total ASCO OVH & BTM | | | | 2763.8 | | | 119.6 | 2322.4 | 227.5 | 94.3 | | |
| Yield (W/o of $C_{10}$ olefin) | | | | | | | 5.2 | 100.5 | 9.8 | 4.1 | | |

TABLE 5-continued

C₁₀ Internal Olefin Catalyst Recycle Study Material Balance

| No. Of Times Catalyst Is Cycled | CHARGE WT. Olefin | CHARGE WT. Recycle | Product Wt. (g) | ASCO DISTILLATION OVH | ASCO DISTILLATION BTM | (g.) L-H | ASCO OVERHEAD COMPOSITION (g) Hydrocarbon | ASCO OVERHEAD COMPOSITION (g) Aldehyde | ASCO OVERHEAD COMPOSITION (g) Alcohol | ASCO OVERHEAD COMPOSITION (g) Unknown | REACTION Time (Hr) | REACTION Conv. % |
|---|---|---|---|---|---|---|---|---|---|---|---|---|
| | | | | | | | (1) | (2) | (2) | (3) | | |

(1) About ⅓ of this is due to unconverted olefin from the first cycle. The remaining ⅔ due to pendant olefin in the feed and paraffin formed in the hydroformylation.
(2) Total alcohol yield after hydrogenation of aldehyde = 111.5 w/o (Theory = 122.9)
(3) Heavy products identify unknown.

Thus the yield of alcohol from the process was equivalent to 1.2 gram per gram of feed olefin or 91 percent of the theoretical yield. If impurities in the feed and unconverted internal olefins are accounted for the yield of alcohol exceeds 95%.

EXAMPLE 3

The effect of temperature and catalyst concentration on the product distribution was determined in a series of experiments. A significant effect of temperature is seen in the isomeric distribution of the product. At the higher temperatures the olefin isomerizes. As a result, all possible isomeric aldehydes are formed, even though a single internal isomeric olefin was used initially. At the highest temperatures where extensive isomerization occurs, the process becomes even more selective towards the production of more linear isomers. Furthermore, the amount of linear aldehyde formed, is much higher than would be expected from an equilibrium mixture of olefin isomers.

The effect of rhodium concentration is in Table 3. Items B and C in this table refer to experiments which differed only in the rhodium catalyst concentration and yet the product distribution between these experiments were remarkably different. This shows that were the rhodium catalyst concentration is maintained in small amounts as it is in the instant invention, an overall and relatively more linear product is obtained. In order for this particular distribution of the product to be maintained, however, it is necessary that both catalyst concentration and temperature be maintained in the ranges provided for in this invention. Variation of either condition outside of the ranges provided for will cause the product distribution to alter and there will be a general loss of overall linearity in the product. This effect can be noted in experiment F under Table 3 where the rhodium concentration is increased to 44 parts per million at 170 degrees where one would ordinarily have a very linear product, if the combination of small rhodium concentration and high temperature had been maintained.

TABLE 3
EFFECT OF REACTION TEMPERATURE ON PRODUCT DISTRIBUTION

| EXPT # | Rh Conc (ppm) Based on Internal Olefin Feed | Temp °C. | ISOMERIC ALDEHYDE DISTRIBUTION Linear | 2-Me—Br | 2-Et—Br | 2-Pr+Br |
|---|---|---|---|---|---|---|
| A | 25 | 100 | 0.2 | .3 | 0.2 | 99.3 |
| B | 25 | 130 | 2.9 | — | 8.3 — | 88.8 |
| C | 5 | 130 | 6.2 | 11.2 | 8.2 | 74.4 |
| D | 5 | 140 | 9.7 | 14.0 | 8.5 | 67.8 |
| E | 5 | 150 | 15.4 | 19.5 | 10.1 | 54.9 |
| F | 44 | 170 | 1.0 | 1.6 | 1.7 | 95.7 |

Reaction Conditions:
Olefin-7-Tetradecene
2-Me—Br is 2-methyl branched aldehyde
Rhodium Source-Rh₂O₃5H₂O
2-Et—Br is 2-ethyl branched aldehyde
Ligand-4:1 mole ratio of triphenyl phosphite
2-Pr+Br is 2-propyl and higher (including butyl, pentyl etc.) branched aldehyde
Pressure-900–950 psig of 1:1 H₂CO
A 2:1 mole ratio of trioctyl phosphine as a ligand.

The instant invention provides for the conversion of internal olefins to alcohols. A vital aspect of this invention is that in carrying out the hydroformylation, the rhodium catalyst concentration must be maintained under 20 parts per million of rhodium based on olefin. In addition to this, the temperature must be maintained over 145° C., and finally with the temperatures in this high a range it is necessary that pressures be maintained over 750 psig. When these conditions are maintained, a more highly linear product is obtainable. Furthermore, when the rhodium catalyst is re-cycled from the distillation step, the catalyst, surprisingly, is more active than it was originally.

In summary, my process can provide an alcohol yield of at least 85 percent, preferably at least 90 percent, based on olefin feed.

Thus, having described the invention in detail, it will be understood by those skilled in the art that certain variations and modifications may be made without departing from the spirit and scope of the invention as defined herein and in the appended claims.

I claim:

1. A process for preparing alcohols from internal $C_4$–$C_{30}$ olefins wherein said process comprises:
   (a) contacting said olefins with hydrogen and carbon monoxide in the presence of a ligand modified recycled rhodium catalyst where the rhodium is present in quantities less than 20 parts per million based on the total charge, and is greater than 0.1 parts per million based on total charge, at a temperature in the range of about 145° C. to about 180° C. and a pressure in the range of about 750 to about 2000 psig to form a reaction product containing a substantial amount of linear and 2-methyl branched aldehydes, (b) separating the reaction product of step (a) from the rhodium catalyst by flash vacuum distillation, (c) hydrogenating the distilled reaction product of step (b) using an effective amount of hydrogenation catalyst at a temperature in the range of about 100° to about 170° C. and a pressure in the range of about 200 to about 2000 psig to produce a crude alcohol mixture, (d) fractionally distilling the crude alcohol mixture of step (c) to remove small amounts of light and heavy impurities and obtain a fraction containing a major amount of alcohols and minor amounts of carbonyl compounds, (e) hydrogenating the fraction containing alcohols and carbonyls using the conditions of step (c) to convert the carbonyl compounds to alcohols and thereby obtaining an alcohol product containing one carbon atom more than the starting olefins, and (f) recycling the product-catalyst bottoms from step (b) to step (a).

2. The process of claim 1 wherein:

(a) in step (a) the ligand contains a trivalent atom, which is phosphorous, arsenic or antimony, and possesses one available pair of electrons;

(b) in step (a) the rhodium is $Rh_2O_3 \cdot 5H_2O$, $Rh_2O_3$ or $RhO_2$, (c) in step (a) the molar amount of ligand to rhodium is about 0.5:1 to 10:1, (d) in step (a) the hydrogen to carbon monoxide mole ratio is in the range of about 0.5 to about 2.1, (e) in step (c) the hydrogenation catalyst is nickel and the amount of catalyst expressed as grams aldehyde liquid/gram catalyst/hour is in the range of about 0.5 to about 2.0, and (f) recycling the product-catalyst bottoms from step (b) to step (a).

3. The process of claim 2 wherein the ligand of step (a) is a triarylphosphite or trialkylphosphine.

4. The process of claim 3 wherein in the step (a) the temperature is in the range of about 145° to about 165° C. and the pressure is in the range of about 850 to about 1200 psig.

5. The process of claim 4 wherein in step (c) the temperature is in the range of about 120° to about 150° C. and the pressure is in the range of about 800 to about 1200 psig.

6. The process of claim 5 wherein:

(a) the amount of rhodium catalyst in step (a) is in the range of about 5 to about 15 parts per million of rhodium based on the olefin, and (b) in step (a) the molar amount of ligand to rhodium is about 2:1 to 4:1, (c) the amount of nickel catalyst, expressed as grams aldehyde liquid/gram catalyst/hour is in the range of about 0.8 to about 12.

7. The process of claims 3 or 6 wherein the ligand is triphenyl phosphite.

8. The process of claims 1, 3, 5, or 6 wherein the olefin of step (a) contains from about 6 to about 15 carbon atoms.

* * * * *